(12) United States Patent
Baldewein et al.

(10) Patent No.: US 7,520,185 B2
(45) Date of Patent: Apr. 21, 2009

(54) SENSOR HANDLE ASSEMBLY

(75) Inventors: Jury Baldewein, Poing (DE); Yaacov Nitzan, Hertzelial (IL)

(73) Assignees: Depuy Orthopadie-Germany (DE); Biosence Webster (Israel) Ltd. (IL)

( * ) Notice: Subject to any disclaimer, the term of this patent is extended or adjusted under 35 U.S.C. 154(b) by 0 days.

(21) Appl. No.: 11/689,297

(22) Filed: Mar. 21, 2007

(65) Prior Publication Data
US 2007/0256508 A1    Nov. 8, 2007

(30) Foreign Application Priority Data
Mar. 23, 2006    (GB)    ................. 0605793.9

(51) Int. Cl.
*G01L 5/06* (2006.01)
*A61B 1/00* (2006.01)
*G01N 3/08* (2006.01)

(52) U.S. Cl. .................. 73/862.393; 600/131; 600/149; 73/826; 73/828

(58) Field of Classification Search .................... 73/826, 73/862.393, 828, 829, 830; 600/131
See application file for complete search history.

(56) References Cited

U.S. PATENT DOCUMENTS

| | | | | |
|---|---|---|---|---|
| 5,391,199 A | * | 2/1995 | Ben-Haim | 607/122 |
| 5,443,489 A | * | 8/1995 | Ben-Haim | 607/115 |
| 6,179,826 B1 | | 1/2001 | Aebischer et al. | |
| 6,499,488 B1 | * | 12/2002 | Hunter et al. | 128/899 |
| 6,690,963 B2 | * | 2/2004 | Ben-Haim et al. | 600/424 |
| 7,394,023 B2 | * | 7/2008 | Rizzuto, Jr. | 174/92 |
| 2001/0032517 A1 | * | 10/2001 | Reinemann et al. | 73/826 |
| 2003/0120150 A1 | * | 6/2003 | Govari | 600/424 |
| 2005/0245821 A1 | * | 11/2005 | Govari et al. | 600/429 |
| 2006/0095030 A1 | * | 5/2006 | Avitall et al. | 606/41 |
| 2006/0189898 A1 | * | 8/2006 | Nitzan et al. | 600/587 |
| 2006/0190009 A1 | * | 8/2006 | Revie et al. | 606/129 |
| 2006/0285861 A1 | * | 12/2006 | Avevor et al. | 439/501 |

FOREIGN PATENT DOCUMENTS

GB    2323265 A    *    9/1998

OTHER PUBLICATIONS

GB 0605793.9 The British Thomson Houston Company Ltd. UK Search Report dated Jul. 17, 2006 1 page.

* cited by examiner

*Primary Examiner*—Harshad Patel
*Assistant Examiner*—Jonathan Dunlap

(57) ABSTRACT

A sensor assembly for use in a surgical procedure is described. The assembly can includes a sensor for implantation into a body part, a sensor cord attached to and extending from the sensor and a handle fastened to the sensor cord. The handle is fastened so that a force can be applied to the sensor cord via the handle. The handle comprises a force indicator to which force applied to the sensor cord is applied and which can provide an indication of the force applied to the sensor cord via the handle.

17 Claims, 2 Drawing Sheets

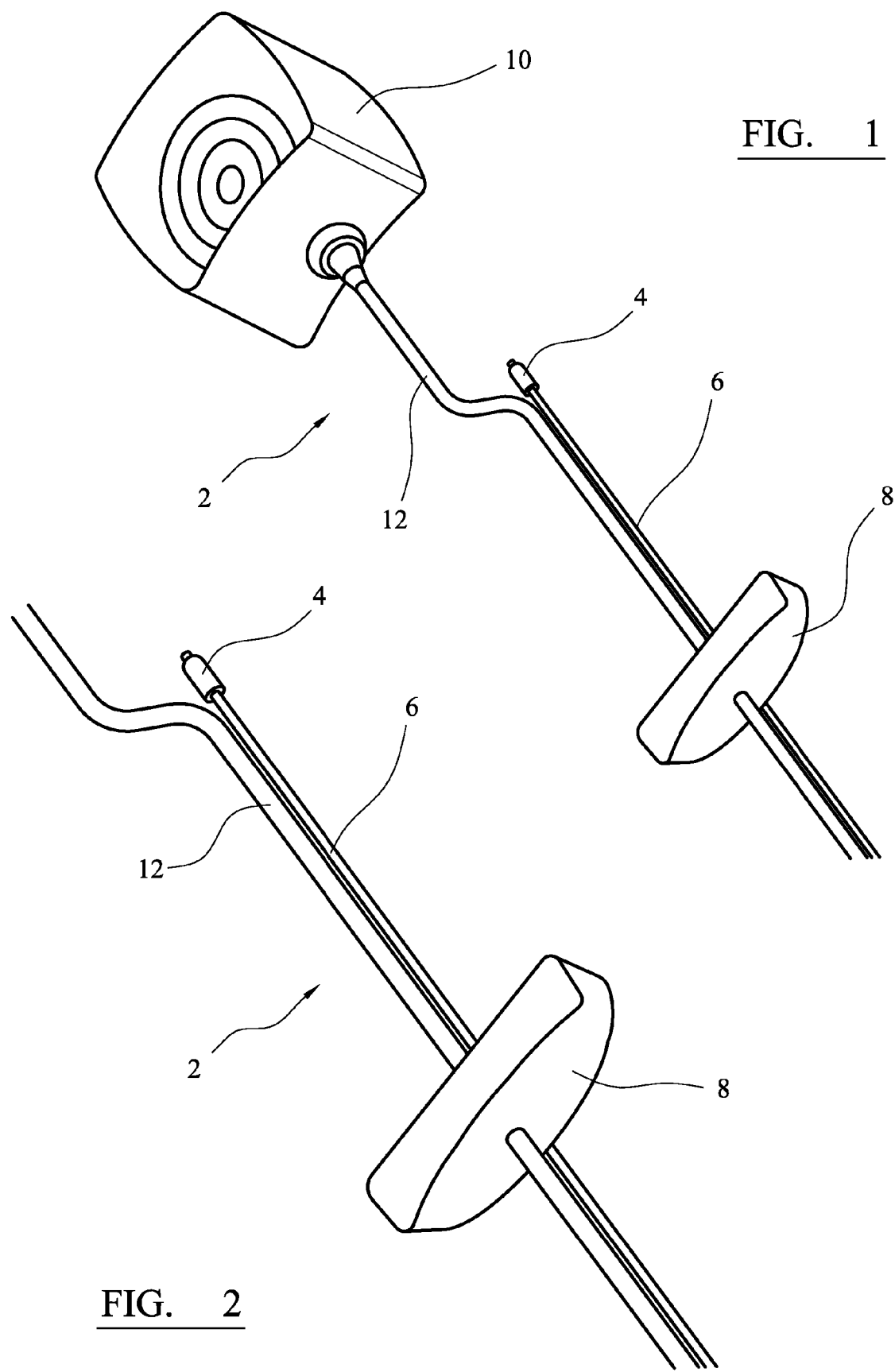

SENSOR HANDLE ASSEMBLY

The present invention relates to a sensor assembly, and in particular to a sensor assembly which provides for the removal of a sensor implanted in a body part by pulling on a cord attached the sensor.

Sensors which can be implanted into a body part of a patient can be used in surgical procedures for many applications. For example, implantable sensors can be used for measuring the temperature of a body part in which the sensor is located, and for measuring the amount of stress a body part is under. In particular, a sensor can be used to provide a registration mark whose location can be determined and tracked by a tracking system. Such a sensor can be implanted in a body part, such as a bone, so that the position of the bone can be tracked, e.g. during a surgical procedure.

When the sensor is used as a marker, a system in which the sensor is incorporated can be used to track the location of the sensor. This can be achieved using electromagnetic techniques. U.S. Pat. Nos. 5,391,199 and 5,443,489 provides details of systems which are applicable to the present invention, in which the coordinates of an intrabody probe are determined using one or more field transducers, such as a Hall effect device, coils, or other antennae carried on the probe. Such systems are used for generating location information regarding a medical probe or catheter. A sensor, such as a coil, is placed in the probe and generates signals in response to externally-applied magnetic fields. The magnetic fields are generated by magnetic field transducers, such as radiator coils, fixed to an external reference frame in known, mutually-spaced locations. Systems which are concerned with tracking a sensor in a three-dimensional space are also disclosed in WO-96/05768, U.S. Pat. No. 6,690,963 and US-A-2002/0065455. Subject matter that is disclosed in the specifications of the patents and patent applications referred to in this paragraph is incorporated in this specification for all purposes by these references.

Implantable sensors are typically implanted immediately prior to a surgical procedure and can subsequently be removed immediately after the completion of the procedure. An implantable sensor of this kind can have a jacket that can be deformed inwardly so as to allow the implantable sensor to be pushed into a previously prepared hole in the bone. Such sensors can have a cord extending from one of its ends. The cord can contain electrical wires which can be connected to a computing device to receive data or location information from the sensor. The sensor can be removed by pulling on the cord attached to the end of the sensor with a sufficient force along the axis of the sensor. Sensors which can be implanted into a body part by being pushed into a prepared hole, and subsequently removed by pulling on a cord attached to the end of the sensor are disclosed in PCT application no. PCT/GB2006/000600. Subject matter that is disclosed in the specification of that patent application is incorporated in this specification for all purposes by this reference.

It is important that the sensor and/or the cord are not damaged by pulling on the cord during removal of the sensor from the body part.

According to a first aspect of the invention there is provided a sensor assembly for use in a surgical procedure, comprising: a sensor for implantation into a body part; a sensor cord attached to and extending from the sensor; and a handle fastened to the sensor cord so that a force can be applied to the sensor cord via the handle, the handle comprising a force indicator to which force applied to the sensor cord is applied, which can provide an indication of the force applied to the sensor cord via the handle.

Providing an indication of the force applied to the sensor cord enables the surgeon to know when a force which is likely to damage the sensor and/or the sensor cord is applied to the sensor cord. Accordingly, as the force indicator can indicate the amount of force applied to the sensor cord, the surgeon can take preventative action to reduce some or all of the force applied to the cord so as to avoid damage to the sensor and/or the sensor cord.

The sensor cord can be used as a guide for locating the location of the sensor in a body part. The sensor cord can snap or become detached from the sensor if too much force is applied during removal. When this happens, not only is it no longer possible to remove the sensor by pulling on the cord, but also it can be difficult to locate the sensor in the body part because the cord can not longer be used as a guide. Accordingly, as the force indicator can provide an indication of the force applied to the sensor cord, the surgeon can take preventative action to reduce the amount of force applied to the cord so as to avoid snapping the sensor cord.

It is also an advantage of the present invention that the surgeon is able to apply a force to the cord by gripping the handle, rather than by gripping the cord. The cord can have a small diameter which can be difficult to grip, and also can cause damage to the surgeons gloves or hands when applying large forces to the cord.

The sensor can collect data relating to the body part. For example, the sensors can be used for measuring the temperature of a body part in which the sensor is located. Optionally, the sensor can be used to measure the amount of stress a body part is under.

Preferably, the sensor can be adapted to be tracked by a tracking system. Preferably, the sensor can be trackable by an electromagnetic tracking system. Preferably, the sensor includes at least one sensing coil which can generate a signal in response to an electromagnetic field generated by a generator coil or coils of a tracking system. Preferably, the sensor is able to provide position information in multiple degrees of freedom, including up to six degrees of freedom. It can be preferred for the sensor of the present invention to provide position information in three degrees of freedom and/or orientation information in three degrees of freedom. Less detailed information can be appropriate for some applications, for example at least three degrees of freedom, preferably at least four degrees of freedom, more preferably at least five degrees of freedom.

Preferably, the sensor comprises three mutually perpendicular coils which can generate electrical signals via induction owing to the location of the sensor in a time varying magnetic field. Preferably, the signals generated by the coils are proportional to the strength of three perpendicular components of the magnetic field, from which the position of the sensor part in the magnetic field and the orientation of the sensor can be determined.

The sensor cord can include a wire or wires for carrying an electrical signal or signals which can be connected to, and allow communication between, the sensor and an external device. The cord can carry power to the sensor where this is required in order for the sensor to produce a signal.

A wire which extends from the sensor can carry a signal from the sensor to an external component. For example, the signal can be carried to a system controller, in particular which is able to analyse the signal. The wire can extend from the sensor to an external pad which can be fastened to the patient's skin or to another convenient surface, for example on the operating table. Preferably, the sensor generates a field when it is within a magnetic field which is generated by a local magnetic field generator provided on a pad which is adapted to be affixed to a surface of the body of the patient. The pad can include a plurality of concentric orthogonal magnetic field generating coils. A driving antenna can be provided to radiate a radio frequency (RF) electromagnetic field. The pad can include a power coil which is coupled to receive the RF electromagnetic field and thereby to provide power for generating the magnetic field. Alternatively, the pad can include an internal power source to provide power for generating the magnetic field. It can however be particularly preferred for the pad to be connected by means of conductors to a source of electrical power.

A local magnetic field generator which is provided on a pad can be used in conjunction with the sensor of the sensor assembly of the invention, when the sensor is implanted in a patient's body, to provide information about the patient, in particular as to the location and orientation of the part of the body in which the sensor is implanted.

Tracking systems which comprise a pad by which a magnetic field can be generated and at least one position transducer or sensor are disclosed in U.S. patent application Ser. No. 11/062,258 filed on 22 Feb. 2005. Subject matter that is disclosed in the specification of that patent application is incorporated in this specification for all purposes by these references.

Preferably, the force indicator provides and indication which can be felt by the user as a result of holding the handle when the pulling force exceeds a predetermined force. This is advantageous because the user can know when the predetermined force has been exceeded without having to look at the sensor assembly. Accordingly, the surgeon can focus his vision elsewhere.

Preferably, the force indicator can reduce the force applied to the sensor cord via the handle when the pulling force exceeds the predetermined force. This reduction in the force applied to the sensor cord can be felt by the user because although the force applied to the sensor cord is reduced, the user will still be applying the same amount of force to the handle and therefore the handle will suddenly accelerate.

The force indicator can reduce the force applied to the sensor cord upon exceeding the predetermined force in a number of different ways. For example, the force indicator can comprise a mechanism which is configured to normally clamp the sensor cord, but is configured to release the cord upon the predetermined force being exceeded.

Preferably, the force indicator comprises a component in the handle, the component having a line of weakness which breaks when the pulling force exceeds the predetermined force, thereby reducing the force applied to the sensor cord. Preferably, the line of weakness is configured such that it breaks when the pulling force exceeds the predetermined force so as to free at least a length of the cord from within the handle, thereby reducing the force applied to the sensor cord. Preferably, the line of weakness if provided at the point or points the component is mounted to the handle.

The sensor cord can be clamped to the force indicator so that the sensor cord cannot slide relative to the force indicator. Accordingly, when the mounting between the force indicator component and the handle breaks, the sensor cord can slide relative to the handle but not to the force indicator component. The handle can enclose the force indicator component and the handle and the force indicator component can be configured such that the force indicator component cannot be removed from within the handle. Accordingly, when the mounting between the component and the handle breaks, the sensor cord can slide relative to the handle by the distance by which the force indicator component is able to move within the handle. Accordingly, the user will experience a temporary acceleration of the handle relative to the sensor cord.

Preferably, the sensor cord is not clamped to the force indicator component. Preferably, the sensor cord can extend around and engage, at least a part of the force indicator component. Preferably, the force indicator component is configured so that when the mounting between the component and the handle breaks, the path the sensor cord takes through the handle is reduced, thereby allowing at least a temporary reduction in the force applied to the sensor cord.

Preferably, the handle clamps the sensor cord on the side of the force indicator that is opposite to end of the handle proximal the sensor. Accordingly, preferably that the portion of the sensor cord on the side of the handle distal to the sensor is not free to slide through the handle. This is advantageous because it can ensure that the handle is not free to slide along the entire length of the sensor cord. This can be important to ensure that even once the force indicator component has broken from the handle it is still possible to apply a force to the sensor cord via the handle. Further, this ensures that upon exceeding the predetermined force, the handle will quickly accelerate and then decelerate, providing the user with a shock sensation.

The force indicator component can be formed as one piece with the handle. For example, the handle and the force indicator component can be formed by a moulding process. Preferably, the component is formed separately from the handle. This can be advantageous as it can allow the use of different force indicator components having different properties, within the handle. For example, the line of weakness between the handle and the force indicator component can be provided by the strength of the force indicator component itself In some instances it might be preferable to use a weaker force indicator component with a certain types of cord.

Preferably, the component is a pin extending between the walls of the handle. Preferably, the pin has a radius and the sensor cord is arranged to extend around the pin's axis. It can be preferable to provide a pin with a rounded cross-sectional shape so as to reduce pressure points on the sensor cord where the sensor cord engages the force indicator component. Preferably, the cross-sectional shape of the pin is circular.

The line of weakness can be provided at any point along the length of the pin. For example, the line of weakness can be provided at the middle of the pin so that it breaks into two upon exceeding the predetermined force.

Preferably, the pin comprises a body portion which the sensor cord engages, and first and second arms at either end of the body portion for engaging the handle. Preferably, the first and second arms are structurally weaker than the body portion of the pin. Accordingly, preferably the first and second arms provide first and second lines of weakness between the pin and the handle. Preferably, the pin is provided as a single moulded piece, wherein the thickness of the arms is less than the thickness of the body part of the pin.

Preferably, the force indicator can provide a visual indication of the pulling force applied to the sensor cord. Accordingly, preferably at least a part of the force indicator is visible from outside the handle. This can be advantageous because in some instances the user might want a visual indication of the pulling force applied to the sensor cord rather than a indication which can be felt through the handle. Preferably, the force indicator provides a visual indication of when a predetermined force has been exceeded. Optionally, the force indicator can provide an indication of the magnitude of the force applied to the sensor cord.

Preferably, the force indicator comprises a resilient member which can be deformed by the application of a force to the sensor cord via the handle. Accordingly, preferably the deformation of the resilient member is visible from outside the handle. In this case, the deformation of the resilient member can provides a visual indication of the force applied to the sensor cord. Preferably, at least one of the resilient member and the handle comprise a marker which can indicate when the force on the sensor cord exceeds the predetermined force. For example, the handle can have a window formed in it and the handle and the resilient member can be configured so that the resilient member becomes visible through the window when the force applied to the sensor cord exceeds a predetermined force. Optionally, a mark could be provided on the handle so that the resilient member is aligned with the mark at the point the force applied to the sensor cord exceeds the predetermined force.

Preferably, the resilient member is a spring member. More preferably, the resilient member is a coil spring.

Optionally, the force indicator can provide a visual indication, as well as an indication which can be felt by the user as a result of holding the handle, when the pulling force exceeds a predetermined force.

The force indicator can be an electronic component which can detect the force applied to the sensor cord, and can output a signal when the force exceeds a predetermined force. The output signal can be a visual signal. The output signal can be an audible signal. The output signal can be a signal which can be felt by the user as a result of holding the handle. The output signal can be a combination of any of those aforementioned output signals.

The predetermined force can be any magnitude of force which is desirable to avoid exerting on the sensor cord and/or sensor. The predetermined force will depend greatly on a number of factors, including the type of the sensor and sensor cord used in the sensor assembly. The predetermined force can be approximately equal to the tear force of the sensor cord. Preferably, the predetermined force is slightly less than the tear force of the sensor cord. Preferably, the predetermined force is not more than 99% of the tear force of the sensor cord, more preferably not more than 95% of the tear force. The tear force of the sensor cord will vary depending on a number of factors, such as the dimensions and material of the sensor cord. The tear force can be the maximum stress which can be applied to the sensor cord before it begins to plastically deform. The tear force can be the breaking stress of the sensor cord. When the sensor cord contains wires, the tear force can be the force at which the wires, or their connection to the sensor will be damaged by the force on the sensor cord.

Preferably, the sensor includes at least one sensing coil which can generate a signal in response to an electromagnetic field. Preferably, the sensor cord includes at least one wire connected to an external device for receiving signals from the sensor. Preferably, the assembly further comprises a patch transmitter for generating the electromagnetic field. Preferably, the assembly further comprises a patch cord, attached to and extending from the patch transmitter. Preferably, the patch cord extends through the handle. Preferably, the patch cord is clamped to the handle so that it cannot slide through the handle.

Preferably, the handle and the patch transmitter have interengaging formations which enable them to be fastened to each other. This can be advantageous because it can allow them to be attached to each other during removal of the sensor, thereby allowing removal of the sensor using one hand.

An embodiment of the invention will now be described in detail, by way of example only and with reference to the accompanying drawings, in which:

FIG. 1 shows a perspective view of a sensor assembly according to the present invention;

FIG. 2 shows a perspective of the sensor, sensor cord and handle of the sensor assembly as shown in FIG. 1;

Figure 3:
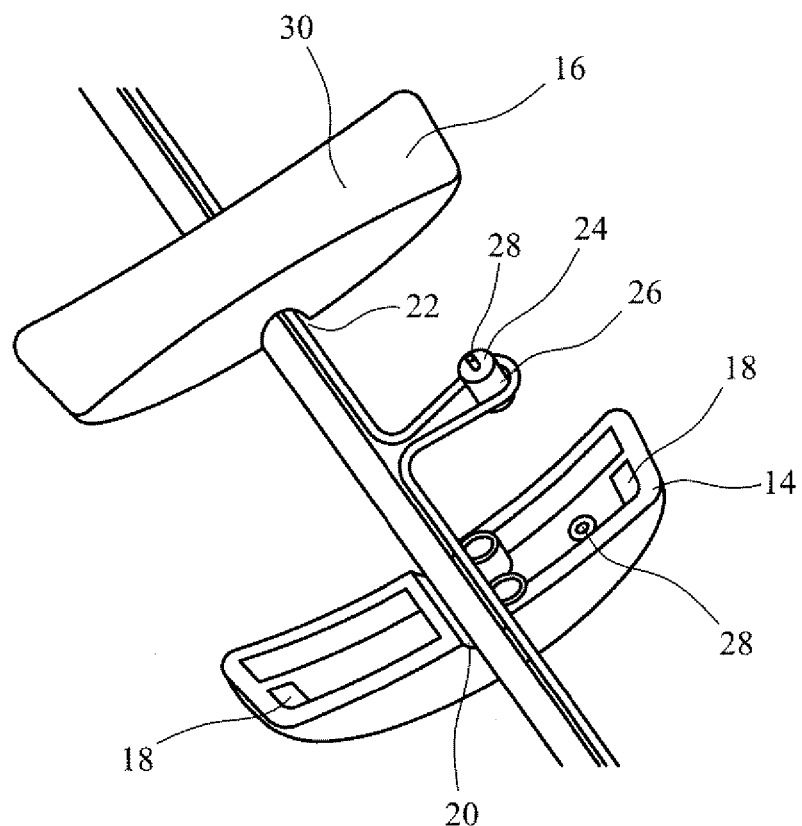
FIG. 3 shows an exploded view of the handle shown in FIG. 1.

Referring to the drawings, FIGS. 1 and 2 shows a perspective view of a sensor assembly 2 according to the invention. The sensor assembly 2 comprises a sensor 4, a sensor cord 6 attached to and extending from the sensor, and a handle 8 fastened to the sensor cord 6 so that a force can be applied to the sensor cord via the handle.

In the particular embodiment described, the sensor can be tracked by a tracking system in order to track the location of the body part in which the sensor is implanted. However, as will be understood, and as described above, the sensor assembly can be used with other sensors used for different purposes.

In the embodiment described, the assembly further comprises a patch transmitter 10 which can generate a time varying electromagnetic field. Power is provided to the patch transmitter 10 from an external device via patch cord 12.

The sensor 4 comprises three mutually perpendicular coils which can generate electric signals by induction owing to the location of the sensor in the time varying electro-magnetic field generated by the patch transmitter 10. The signals generated by the coils are proportional to the strengths of the three perpendicular components of the magnetic field, from which the position of the sensor in the magnetic field and the orientation of the sensor can be determined. The two ends of each coil are soldered to a contact pad towards the free end of the sensor. The sensor may be a Hall effect device, coils or other antennae which can be contained in the sensor. An example of a suitable coil sensor is disclosed in US-A-2003/0120150 (Govari). The disclosed sensor includes at least one sensing coil which can generate a signal when it moves within an electromagnetic field transmitted by a local transmitter. The disclosed coil sensor is able to provide position information in multiple degrees of freedom, including up to six degrees of freedom. It can be preferred for the sensor of the present invention to provide position information in six degree of freedom, although less detailed information can be appropriate for some applications, for example at least three degrees of freedom, preferably at least four degrees of freedom, more preferably at least five degrees of freedom.

In the embodiment described, the sensor cord 6 includes a central load bearing core. Arranged around the core are three twisted pairs of insulated copper wire. Each twisted pair carries an electrical signal from a respective one of the coils in the sensor. Each wire of the twisted pair is attached to respective contact pads for respective coils to provide electrical communication between the signals generated by the sensor coils and the cord.

An appropriate sensor and sensor cord which can be used in the assembly of the present invention are disclosed in PCT application no. PCT/GB2006/000600. Subject matter that is disclosed in the specification of that patent application is incorporated in this specification for all purposes by this reference.

Figure 4:
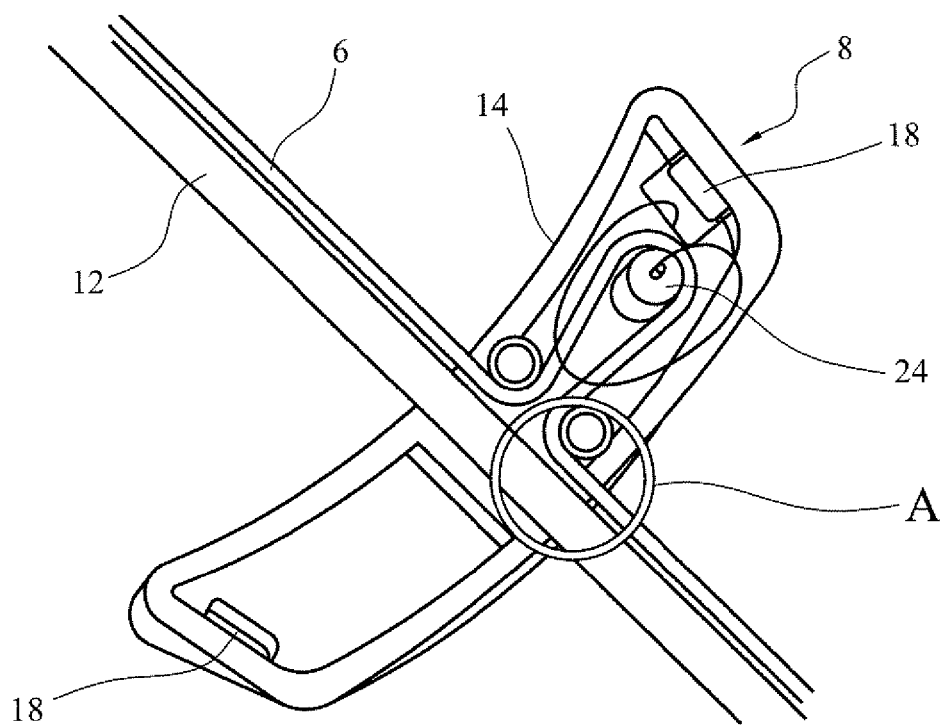
FIG. 4 shows the handle shown in FIG. 1 without the second part of the handle.

As best shown in FIGS. 3 and 4, the handle 8 comprises first 14 and second 16 shell bodies which can be clipped together via releasable attachment means on the first shell body (18) and the second shell body (not shown). The first 14 and second 16 shell bodies include first 20 and second 22 recesses respectively. When the first 14 and second 16 shell bodies are assembled, the first 20 and second 22 recesses define a channel through which the sensor cord 6 and patch cord 12 can extend.

The handle 8 further comprises a force indicator component in the form of a pin 24. The pin 24 comprises a body part 26 and first 28 and second (not shown) arms extending from either end of the body part 26. The body part 26 and the arms 28 are generally cylindrical in shape. The diameter of the first 28 and second arms is less than the diameter of the body part 26. The pin 24 is formed as a single component and the arms 28 and body part 26 are formed from the same material. Accordingly, the first 28 and second arms are structurally weaker than the body part 26.

The first 14 and second 16 shell bodies comprise first 28 and second 30 bores for receiving the second and first 28 arms of the pin 24 respectively. Accordingly, the pin 24 extends between and is held in position within the handle by the first 14 and second 16 shell bodies once they are clipped together.

The patch cord 12 extends straight through the channel defined by the recesses 20 and 22 of the first 14 and second 16 shell bodies. The sensor cord 6 is looped around the body part 26 of the pin 24. Accordingly, due to the tortuous path taken by the sensor cord 6 through the handle 8, the length of sensor cord within the handle 8 is greater than the width of the handle taken in the direction generally parallel to the axis of the sensor cord between the sensor 4 and the handle 8.

The sensor cord 6 is free to slide through the opening defined by the recesses 20 and 22 of the first 14 and second shell bodies, at the end of the handle proximal to the sensor 4. The sensor cord 6 is clamped by the handle at the point the sensor cord 6 exits the handle on the end distal to the sensor 4, indicated by region A, so that the sensor cord 6 cannot slide through the handle at region A.

In use, the sensor 4 is push implanted into a pre-formed hole in a body part (not shown). To remove the sensor 4 from the body part, a force is applied to the handle 8 so as to pull the handle away from the sensor 4. The sensor cord 6 is prevented from sliding through the handle due to the sensor cord being clamped to the handle 8 at region A.

Accordingly, the pulling force applied to the handle is applied to the sensor cord 6. Due to the sensor cord 6 being looped around the pin 24, the force on the sensor cord 6 tends to pull the pin 24 towards the channels 20 and 22 of the first 14 and second 16 shell bodies of the handle 8. When the force exerted on the handle 8 exceeds a predetermined force, that is the breaking force of the first 28 and second arms, the first 28 and second arms of the pin 24 will break from the body part 26. The body part 26 of the pin 24 is then free to move within the handle towards the first 20 and second 22 channels. The movement of the pin 24 reduces the path of the sensor cord 6 through the handle 8, and so a part of the sensor cord 6 will slide through the opening defined by the ends of the first 20 and second 22 channels that are proximal the sensor 4.

As the sensor cord slides through the opening, the force applied to the sensor cord via the handle will be reduced, and the handle will tend to accelerate in the pulling direction. This will continue until the body part 26 of the pin 24 engages the internal walls of the handle 8 to prevent further movement of the body part 26 thereby restricting further sliding of the sensor cord 6 through the opening defined by the ends of the first 20 and second 22 channels that are proximal the sensor 4.

Accordingly, when the force exerted on the sensor cord 6 exceeds a predetermined force, the pin 24 breaks to provide a sudden, but brief movement of the handle, which can be felt by the user as a result of holding the handle.

The invention claimed is:

1. A sensor handle assembly for use in a surgical procedure, comprising:
   a sensor configured to be implanted into a body part;
   a sensor cord attached to and extending from the sensor;
   a handle having an inlet, an outlet and a recess; and
   a component sized and configured to be disposed in the recess at a location between the inlet and the outlet, and wherein a continuous portion of the sensor cord is disposed through the inlet and around the component, such that the length of sensor cord disposed within the recess is greater than the distance measured from the inlet to the outlet, and wherein the component is configured to break when a force exceeding a predetermined force is exerted on the component.

2. The sensor handle assembly of claim 1, wherein the component is configured to provide an indication that can be felt by the user holding the handle when the force exceeding the predetermined force is exerted on the component.

3. The sensor handle assembly of claim 1, wherein the component is configured to cause a reduction in the force applied to the sensor cord via the handle when the force exceeding the predetermined force is exerted on the component.

4. The sensor handle assembly of claim 1, wherein the component has a line of weakness that is configured to break when the force exceeding the predetermined force is exerted on the component.

5. The sensor handle assembly of claim 1, wherein the component is formed separately from the handle.

6. The sensor handle assembly of claim 1, wherein the recess of the handle defines a first wall and a second wall and the component is a pin that extends between the first wall and the second wall.

7. The sensor handle assembly of claim 1, wherein the continuous portion of the sensor cord is disposed through the inlet, around the component and through the outlet.

8. The sensor handle assembly of claim 1, wherein recess forms a channel within which the continuous portion of the sensor cord is disposed, and, when so disposed, a portion of the continuous portion that is disposed within the inlet and around component bends at least 90 degrees within the recess prior to contacting the component.

9. The sensor handle assembly of claim 1, wherein the component comprises a body, a first arm extending from a first end of the body, and a second arm extending from a second end of the body, and wherein at least one of the first arm and second arm are configured to be structurally weaker than the body.

10. The sensor handle of claim 9, wherein the body has a body diameter, and the first arm has a first diameter and the second arm has a second diameter, and at least one of the first diameter and the second diameter is smaller than the body diameter.

11. The sensor handle assembly of claim 1, wherein the predetermined force is approximately equal to the tear force of the sensor cord.

12. The sensor handle assembly of claim 1, wherein the handle is configured to receive a second cord.

13. The sensor handle assembly of claim 12, wherein the handle and second cord are associated with one another such that a force can be applied to the second cord via the handle.

14. The sensor handle assembly of claim 13, wherein the handle, the component and the second cord are configured such that any force applied to the second cord is not applied to the component.

15. The sensor handle assembly of claim 1, wherein the sensor includes at least one sensing coil that can generate a signal in response to an electromagnetic field, the sensor cord includes at least one wire connected to an external device for receiving signals from the sensor, and the assembly further comprises:
   a patch transmitter for generating the electromagnetic field; and a patch cord, attached to and extending from the patch transmitter.

16. The sensor handle assembly of claim 15, wherein at least a portion of the patch cord is disposed within the handle.

17. The sensor handle assembly of claim 16, wherein the patch cord is clamped to the handle.

* * * * *

UNITED STATES PATENT AND TRADEMARK OFFICE
CERTIFICATE OF CORRECTION

| | | |
|---|---|---|
| PATENT NO. | : 7,520,185 B2 | Page 1 of 1 |
| APPLICATION NO. | : 11/689297 | |
| DATED | : April 21, 2009 | |
| INVENTOR(S) | : Jury Baldewein and Yaacov Nitzan | |

It is certified that error appears in the above-identified patent and that said Letters Patent is hereby corrected as shown below:

Title Page, Item (73) Assignee: Biosence should be "Biosense"

Signed and Sealed this
Twenty-eighth Day of June, 2011

David J. Kappos
*Director of the United States Patent and Trademark Office*